United States Patent [19]
Wilk

[11] Patent Number: 5,908,028
[45] Date of Patent: Jun. 1, 1999

[54] CORONARY ARTERY BY-PASS METHOD

[75] Inventor: Peter J. Wilk, New York, N.Y.

[73] Assignee: Wilk Patent Development Corp., New York, N.Y.

[21] Appl. No.: 08/893,643

[22] Filed: Jul. 11, 1997

Related U.S. Application Data

[62] Division of application No. 08/665,950, Jun. 19, 1996, Pat. No. 5,662,124.

[51] Int. Cl.$^6$ ..................................................... A61B 19/00
[52] U.S. Cl. ................................................. 128/898; 606/7
[58] Field of Search ............................... 600/16, 15, 300; 128/898, 897; 606/7, 15, 16

[56] References Cited

U.S. PATENT DOCUMENTS

| | | | |
|---|---|---|---|
| 4,469,098 | 9/1984 | Davi | 128/303.01 |
| 4,658,817 | 4/1987 | Hardy | 128/303.01 |
| 4,785,815 | 11/1988 | Cohen | 128/642 |
| 4,995,857 | 2/1991 | Arnold | 600/16 |
| 4,997,431 | 3/1991 | Isner et al. | 606/15 |
| 5,106,386 | 4/1992 | Isner et al. | 606/15 |
| 5,111,832 | 5/1992 | Saksena | 128/898 |
| 5,287,861 | 2/1994 | Wilk | 128/898 |
| 5,327,913 | 7/1994 | Taheri | 128/898 |
| 5,429,144 | 7/1995 | Wilk | 128/898 |

FOREIGN PATENT DOCUMENTS

| 3718139 | 12/1988 | Germany | 606/15 |
|---|---|---|---|

OTHER PUBLICATIONS

Lee et al. "Effects of Laser Irradiation Delivered by Flexible Fiberoptic System on the Left Ventricular Internal Myocardium" Am Heart J 106(3): 587–590, Sep. 1983.

Cooley et al. "Transmyocardial Laser Revascularization" Texas Heart Instit J 21(3):220–4, 1994

Isner, et al, Lasers: their Potential in Cardioascular Medicine, Cardiovascular Medicine 1985, 23–37, May 1985.

*Primary Examiner*—Mickey Yu
*Assistant Examiner*—Kelly O'Hara
*Attorney, Agent, or Firm*—Knobbe, Martens, Olson & Bear, LLP

[57] ABSTRACT

A cardiovascular treatment method utilizes an elongate flexible surgical instrument (e.g., catheter) having a distal end. A distal end portion of the instrument is inserted into a vascular system of a patient. A surgical head at the distal end of the instrument is positioned so that the head is disposed adjacent to myocardium tissue of the patient. The head is operated to form a recess in the myocardium tissue. Prior to operating the head to form the recess, a thickness of the myocardium tissue is measured, the recess formed during the operation having a length determined in accordance with the measured thickness of the myocardium tissue. The thickness measurement partially determines the length of the recess. The angle of entry of the recess with respect to the heart wall also partially determines the length of the recess: the greater the angle, the longer the recess can be for a given myocardium thickness.

20 Claims, 2 Drawing Sheets

CORONARY ARTERY BY-PASS METHOD

This is a division of application Ser. No. 08/665,950 filed Jun. 19, 1996 and now U.S. Pat. No. 5,662,124.

BACKGROUND OF THE INVENTION

This invention relates to a method for effectuating a coronary artery bypass.

Coronary arteries frequently become clogged with plaque which at the very least impairs the efficiency of the heart's pumping action and can lead to heart attack. The conventional treatment for a clogged coronary artery is a coronary by-pass operation wherein one or more venous segments are inserted between the aorta and the coronary artery. The inserted venous segments or transplants by-pass the clogged portion of the coronary artery and thus provide for a free or unobstructed flow of blood to the heart.

Such conventional coronary artery by-pass surgery is expensive, time-consuming, and traumatic to the patient. Hospital stay subsequent to surgery and convalescence are prolonged.

A new coronary artery by-pass technique is disclosed in U.S. Pat. No. 5,429,144. That technique utilizes a stent made of a biocompatible material and comprises steps of moving the stent in a collapsed configuration through a blood vessel of a patient's vascular system to the patient's heart, inserting the stent in the patient's myocardium so that the stent extends at least partially through the myocardium and only within the myocardium, and upon the disposition of the stent in the myocardium, expanding the stent from the collapsed configuration to a substantially tubular expanded configuration so that a blood flow path is formed at least partially through the myocardium.

Pursuant to U.S. Pat. No. 5,429,144, the stent may be disposed in the myocardium so that it extends only partially through the myocardium, from a coronary artery, upstream of a vascular obstruction, or from the left ventricle of the heart. Alternatively, the stent may extend completely through the myocardium to establish a blood flow path from the left ventricle to a coronary artery, downstream of a vascular obstruction. In any case, the stent is deployed so that it extends only within the myocardium and does not protrude beyond the heart tissues, either into the left ventricle or into the coronary artery.

Where the stent of U.S. Pat. No. 5,429,144 extends only partially through the myocardium and thus terminates within the cardiac tissues, the stent guides blood directly into the heart tissues and particularly into cardiac vesicles which naturally occur in the myocardium. The blood is naturally distributed from the vesicles into the cardiac tissues and is collected by the veins of the heart. Where the stent terminates within the myocardium and extends from a coronary artery, upstream of a vascular obstruction, the stent maintains its expanded form during diastole, so that blood pumped from the heart is forced into the stent and from thence into the cardiac tissues. Where the stent terminates within the myocardium and extends from the left ventricle, the stent may collapse during systole, under the compressive forces exerted by the contracting heart muscle. In that case, blood is delivered to the myocardium during diastole: blood flows into the stent from the left ventricle as the ventricle is filling with blood. Alternatively, where the stent terminates within the myocardium and extends from the left ventricle, the stent may maintain its expanded form during systole, despite the compressive forces exerted by the contracting heart muscle. In that case, blood is forced into the stent and from thence into the cardiac tissues during heart contraction.

According to U.S. Pat. No. 5,429,144, the coronary bypass method further comprises inserting a distal end portion of a catheter into the perforation or recess prior to the ejection of the stent, and sensing pressure on the catheter along the distal end portion, thereby determining a thickness of the myocardium at the perforation or recess. The stent is cut from a piece of stent material so that the stent has a length corresponding to the sensed or measured thickness of the myocardium at the perforation or recess.

U.S. Pat. No. 5,429,144 describes the use of a drill head during diastole to cut a perforation into the myocardium. The synchronization or coordination of the drilling and stent ejecting steps with heart action is implementable by computer. Where the stent is disposed in the myocardium so that the stent extends only partially through the myocardium from the patient's left ventricle, the stent is inserted into the myocardium from the left ventricle. Accordingly, a distal end of the catheter is passed into the left ventricle prior to the deployment of the stent, while the stent is moved in its collapsed configuration through the catheter and into the left ventricle of the heart.

OBJECTS OF THE INVENTION

An object of the present invention is to provide an improved method for forming a coronary artery by-pass to thereby enable the oxygenation of cardiac tissues.

Another object of the present invention is to provide a method for forming a coronary artery by-pass which does not require leaving a device in the patient.

A further object of the present invention is to provide such a method which is less invasive and less traumatic to the patient than conventional by-pass surgery.

SUMMARY

Basically, the present invention is directed to a stent-less coronary artery by-pass wherein one or more recesses are formed in the myocardium. The recesses open sufficiently during diastole to permit blood flow into the myocardium and the vesicles therein.

A cardiovascular treatment method in accordance with the present invention utilizes an elongate flexible surgical instrument (e,.g. catheter) having a distal end. A distal end portion of the instrument is inserted into a vascular system of a patient. A surgical head at the distal end of the instrument is positioned so that the head is disposed adjacent to myocardium tissue of the patient. The head is operated to form a recess in the myocardium tissue. Prior to operating the head to form the recess, a thickness of the myocardium tissue is measured, the recess formed during the operation having a length determined in accordance with the measured thickness of the myocardium tissue. The thickness measurement partially determines the length of the recess. The angle of entry of the recess with respect to the heart wall also partially determines the length of the recess: the greater the angle, the longer the recess can be for a given myocardium thickness.

The thickness of the myocardium may be measured by generating an ultrasonic pressure wave, sensing reflected pressure waves and analyzing the reflected pressure waves to determine the thickness. The ultrasonic pressure wave generator (e.g., a piezoelectric crystal) and the ultrasonic wave sensor (also a piezoelectric crystal) may be disposed in the catheter wall at the distal tip thereof, or at the distal tip of an ancillary instrument inserted through a lumen of the catheter.

Measuring the thickness of the myocardium may be implemented by operating a computer aided tomography scanning machine, a magnetic resonance imaging machine or an echocardiogram device.

Generally, it is contemplated that the recess terminates in the myocardium tissue and is formed from the left ventricle of the patient. Accordingly, the surgical head is disposed adjacent to an inner side of the myocardium tissue, inside the left ventricle, so that the recess extends from the left ventricle.

According to a feature of the present invention, the surgical head is a contact laser tip. In that case, operating the surgical head includes transmitting monochromatic coherent electromagnetic radiation (laser energy) through the contact laser tip to the myocardium tissue. Alternatively, the surgical head may include a drill tip, the operating of the head including pushing the drill tip into the myocardium tissue and rotating the drill tip during the step of pushing.

DESCRIPTION OF THE PREFERRED EMBODIMENTS

Figure 2:
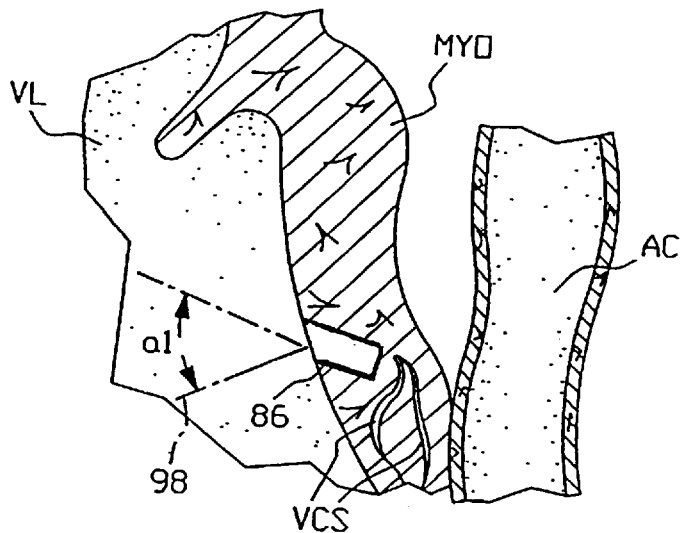
FIG. 2 is a partial cross-sectional view, on a larger scale, showing one of the recesses of FIG. 1.

The present invention seeks to oxygenate the cardiac muscle or myocardium MYO (FIG. 1) where a coronary artery AC is blocked with vascular plaque material VP. To that end, a distal end portion of an angioplastic instrument 12 or 14 (FIGS. 3, 4) is inserted through a femoral artery (not shown) and the aorta AO into the left ventricle VL. More particularly, a distal end of a steerable catheter 16 or 18 (FIGS. 3, 4) is inserted along a predetermined path 92, 94, 96 through the vascular system of the patient and into left ventricle VL. Instrument 12 or 14 is then operated to form a plurality of recesses 86, 88 and 90 in myocardium MYO for providing a plurality of pathways for guiding blood directly into the cardiac tissues from left ventricle VL. Recesses 86, 88, and 90 extend from left ventricle VL and terminate within myocardium MYO. Each recess 86, 88, and 90 thus extends only partially into myocardium MYO.

Figure 3:
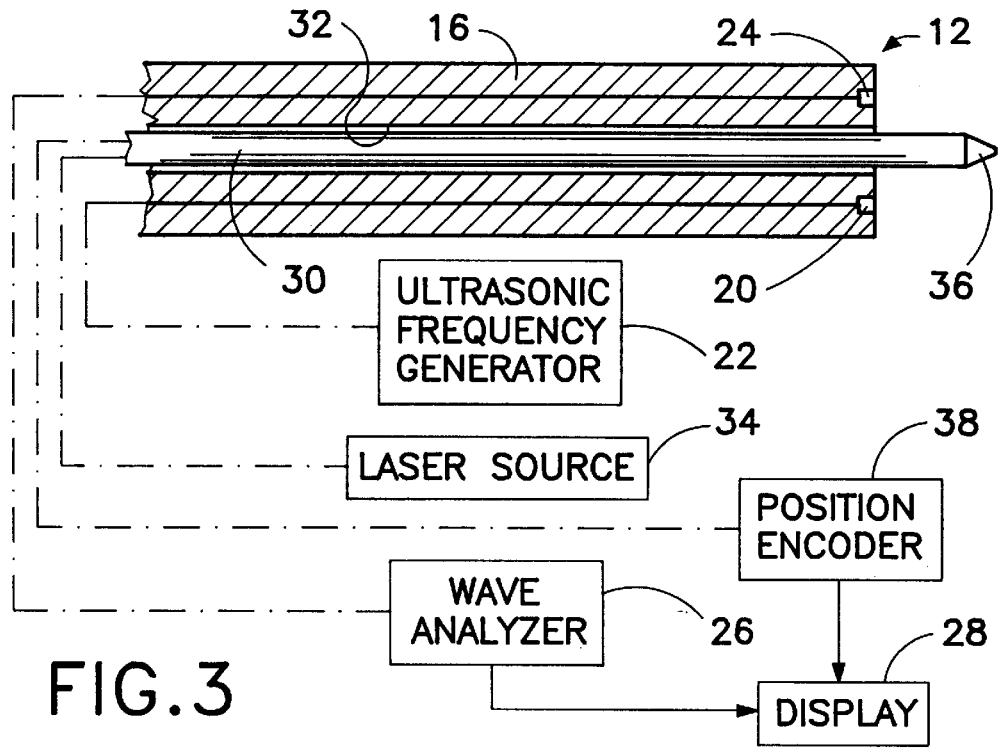
FIG. 3 is partially a schematic longitudinal cross-sectional view and partially a block diagram of an instrument assembly for forming the recesses shown in FIG. 1.

As illustrated in FIG. 3, angioplastic surgical instrument 12 includes a piezoelectric transducer 20 disposed at a distal tip of catheter 16 and electrically connected to an ultrasonic frequency generator 22. Another piezoelectric transducer 24 disposed at the distal tip of catheter 16 is operatively coupled to a wave analyzer 26 which serves to determine the thickness of myocardium MYO upon disposition of the distal end of catheter 16 inside left ventricle VL. Wave analyzer 26 is connected to a display 28 for indicating a computed heart wall thickness to a vascular surgeon.

Figure 1:
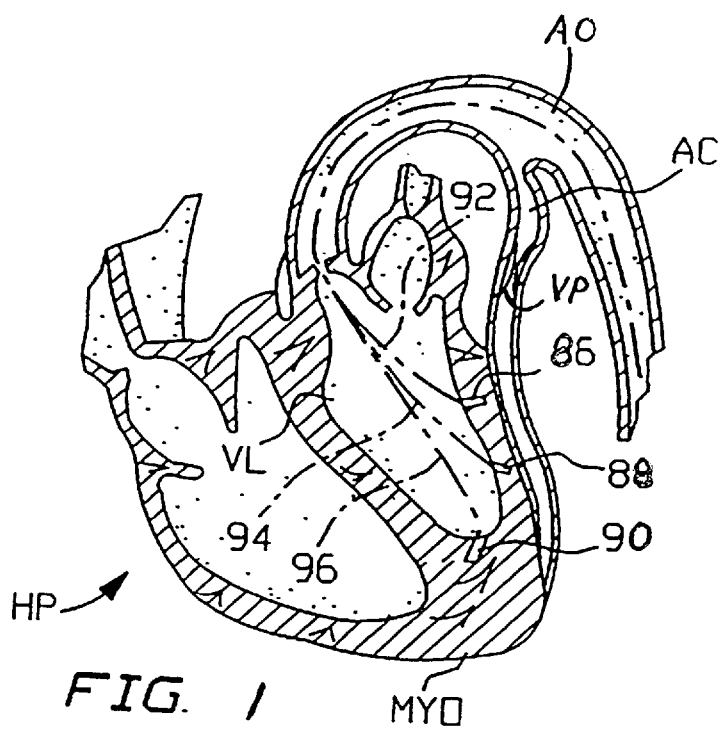
FIG. 1 is a schematic cross-sectional view of a human heart, showing a plurality of recesses formed in the myocardium for providing a plurality of pathways for guiding blood directly into the cardiac tissues from the left ventricle, in accordance with the present invention.

As further illustrated in FIG. 3, an optical fiber 30 is inserted through a lumen 32 of catheter 16. At a proximal end, fiber 30 extends to a laser source 34, while at a distal end fiber 30 is provided with a surgical head in the form of a tapered contact tip 36 of conventional crystalline material. Tip 36 delivers coherent monochromatic electromagnetic radiation from laser source 34 to target tissues of the patient's heart HP (FIG. 1). A position encoder 38 is operatively linked to fiber 30 for measuring a linear displacement of the fiber during the formation of recesses 86, 88, 90. Encoder 38 is connected to display 28 for indicating a measured fiber displacement to a vascular surgeon.

Figure 4:
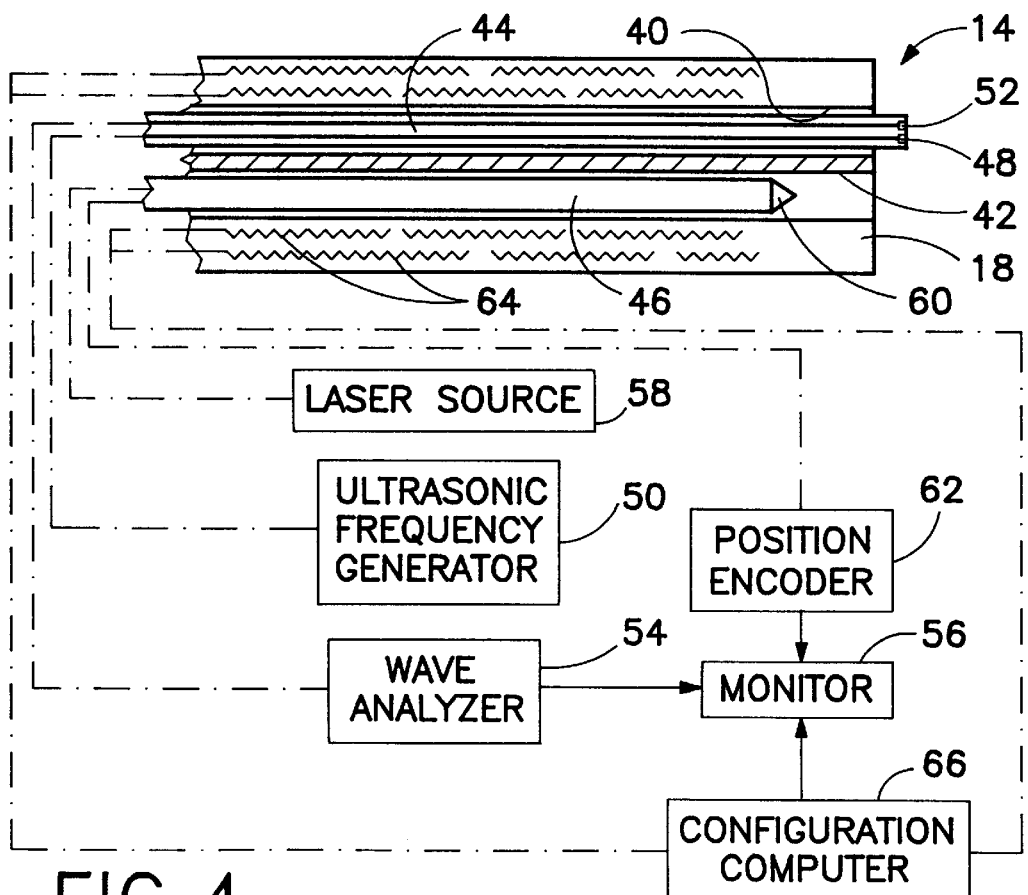
FIG. 4 is partially a schematic longitudinal cross-sectional view and partially a block diagram of another instrument assembly for forming the recesses shown in FIG. 1.

As depicted in FIG. 4, catheter 18 is provided with a pair of lumens 40 and 42 which receive an ultrasonic probe 44 and an optical fiber 46, respectively. Ultrasonic probe 44 includes an electroacoustic piezoelectric transducer 48 disposed at a distal tip of the probe and electrically connected to an ultrasonic frequency generator 50. An acoustoelectric piezoelectric transducer 52 also disposed at the distal tip of probe 44 is operatively coupled to a wave analyzer 54. Analyzer 54 processes reflected ultrasonic wave pressures, sensed by transducer 52, to determine the thickness of myocardium MYO (FIG. 1) upon disposition of the distal end of catheter 18 with probe 44 inside left ventricle VL. The results of the thickness computations of analyzer 54 are transmitted to a monitor 56 for display.

As additionally depicted in FIG. 4, optical fiber 46 extends at one end to a laser source 58 and is provided at an opposite end with a surgical head in the form of a tapered contact tip 60. Tip 60 is made of conventional crystalline material and functions to deliver coherent monochromatic electromagnetic radiation from laser source 58 to target tissues of the patient's heart HP (FIG. 1). A position encoder 62 is coupled to fiber 46 for measuring a linear displacement of the fiber during the formation of recesses 86, 88, 90. Encoder 62 is connected to monitor 56 for indicating a measured fiber displacement.

As further shown in FIG. 4, catheter 18 incorporates in its wall a plurality of strain gauges 64 distributed along the catheter. Strain gauges 64 are operatively connected to a computer or microprocessor 66 which analyzes the signals from the strain gauges to determine the configuration of catheter 18 inside the patient. The computed configuration is displayed on monitor 56, together with an image of internal organs of the patient. The image of the internal organs is produced, for example, by magnetic resonance imaging (MRI), computer aided tomography (CAT) or an echocardiograph.

Upon insertion of the distal end of catheter 16 (FIG. 3) or 18 (FIG. 4) into left ventricle VL and upon the orientation of the catheter tip at a predetermined angle al (FIG. 2) with respect to the perpendicular 98 to the myocardium MYO, an a-c electrical current of ultrasonic frequency is transmitted from generator 22 (FIG. 3) or 50 (FIG. 4) to transducer 20 (FIG. 3) or 48 (FIG. 4) to produce an ultrasonic pressure wave. This pressure wave is reflected from inner and outer surfaces (not designated) of myocardium MYO. The reflected ultrasonic pressure waves are sensed by transducer 24 (FIG. 3) or 52 (FIG. 4) and analyzed by analyzer 26 (FIG. 3) or 54 (FIG. 4) to determine the thickness of myocardium MYO in an area located immediately in front of the distal end of catheter 16 (FIG. 3) or probe 44 (FIG. 4). Provided with cardiac wall thickness information via display 28 (FIG. 3) or monitor 56 (FIG. 4), a vascular surgeon can determine an appropriate length for a recess 86, 88, or 90 to be formed in the myocardium. Recesses 86, 88, and 90 have a length sufficiently large to effectuate artificial cardiac vascularization but small enough to not traverse the myocardium.

Upon the determination of the entry location, entry angle a1 and the depth or length of the recess 86 to be formed, laser fiber 30 (FIG. 3) or 46 (FIG. 4) is ejected from catheter 16 or 18, respectively and contact tip 36 or 60, respectively is placed in contact with the myocardium tissues. Laser energy is transmitted from source 34 (FIG. 3) or 58 (FIG. 4) to form recess 86 at angle a1 in myocardium MYO. Fiber 30 (FIG. 3) or 46 (FIG. 4) is advanced a predetermined distance into myocardium MYO, the distance of penetration of tip 36 (FIG. 3) or 60 (FIG. 4) being ascertained by position encoder 38 or 62.

The formation of recesses 86, 88 and 90 as described hereinabove may be implemented in part via a computer programmed to enable the timing of heart perforation, catheter insertion, and other operations so that those operations are performed only during the diastolic phase of a cardiac cycle. The programming and utilization of a computer in such a procedure will be clear to one skilled in the art from the teachings of U.S. Pat. No. 4,788,975 to Shturman et al., the disclosure of which is hereby incorporated by reference.

As stated above, it is contemplated that laser energy is transmitted along fiber 30 or 46 to form recess 86, 88 or 90 only during a diastolic phase of a cardiac cycle. In some cases, tip 36 or 60 may be left in place in myocardium MYO during a limited number of systolic iterations, to enable completion of recess formation. Alternatively, the contact tip 36 or 60 may be removed during systole and reinserted during diastole until the recesses are formed.

After a cardiac vascularization operation as described above is completed, blood drains into recesses 86, 88, 90 from left ventricle LV and penetrates to vesicles VCS in the myocardium MYO during diastole. The blood is naturally distributed from vesicles VCS into cardiac tissues and is collected by the veins (not shown) of the heart. Even though some of the blood may return to ventricle VL during systole (and from thence to aorta AO), enough blood remains in the myocardium to provide adequate oxygen and nutrients thereto.

In addition to one or more recesses 86, 88, and 90 inserted from the left ventricle VL partially into myocardium MYO, one or more recesses may be formed to connect left ventricle VL with coronary artery AC, as described in U.S. Pat. No. 5,429,144, the disclosure of which is hereby incorporated by reference. As additionally described in U.S. Pat. No. 5,429,144, the formation of recesses 86, 88 and 90 may be implemented with a rotary drill rather than a contact laser. U.S. Pat. No. 5,429,144 also discloses steering componentry which enables an operator to control, from outside the patient, an orientation of the distal tip of catheter 16 or 18 upon insertion of the catheter into the patient.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that the measurement of cardiac wall thickness may be alternatively accomplished via an MRI machine, a CAT scanner or by an echocardiogram. For example, a "measuring rod" of a predetermined length may be inserted through the angioplastic catheter. A computer connected to a CAT-scanner, an MRI machine or other imaging device then automatically determines myocardium thickness by comparing the dimensions thereof to the known length of the "measuring rod". The computer with scanner input may be additionally used to determine optimal locations and insertion angles of multiple stents, e.g., stents 86, 88, and 90.

Accordingly, it is to be understood that the drawings and descriptions herein are preferred by way of example to facilitate comprehension of the invention and should not be construed to limit the scope thereof

What is claimed is:

1. A cardiovascular treatment method comprising the steps of:
   providing an elongate flexible surgical instrument having a distal end;
   inserting a distal end portion of said instrument into a vascular system of a living patient;
   disposing a surgical head at said distal end of said instrument so that said head is disposed adjacent to myocardium tissue of the patient;
   operating said head to form a recess in the myocardium tissue; and
   prior to operating said head to form said recess, measuring a thickness of the myocardium tissue, said recess having a length determined in accordance with the measured thickness of the myocardium tissue.

2. The method set forth in claim 1 wherein measuring said thickness includes generating an ultrasonic pressure wave, sensing reflected pressure waves and analyzing the reflected pressure waves to determine said thickness.

3. The method set forth in claim 2 wherein the generating of said ultrasonic pressure wave includes operating a transducer disposed at said distal end of said instrument.

4. The method set forth in claim 1 wherein measuring said thickness includes operating a magnetic resonance imaging machine.

5. The method set forth in claim 1 wherein measuring said thickness includes operating a computer aided tomography scanning machine.

6. The method set forth in claim 1 wherein measuring said thickness includes taking an echocardiogram.

7. The method set forth in claim 1 wherein said recess terminates in the myocardium tissue.

8. The method set forth in claim 1 wherein said distal end portion is inserted into a left ventricle of the patient, said head being disposed adjacent to an inner side of the myocardium tissue, inside the ventricle, said recess extending from the ventricle into the myocardium tissue.

9. The method set forth in claim 8 wherein said recess terminates in the myocardium tissue.

10. The method set forth in claim 1 wherein said surgical head is a contact laser tip, the operating of said head including transmitting monochromatic coherent electromagnetic radiation through said tip to the myocardium tissue.

11. The method set forth in claim 1 wherein said surgical head includes a drill tip, the operating of said head including pushing said drill tip into the myocardium tissue and rotating said drill tip during said step of pushing.

12. The method set forth in claim 1 wherein the operating of said surgical head is implemented during diastole.

13. The method set forth in claim 12, further comprising operating a computer to synchronize the operating of said surgical head with the rhythm of the heart.

14. The method set forth in claim 1 wherein said surgical head is operated so that said recess extends only partially through the myocardium tissue from a coronary artery of the patient.

15. The method set forth in claim 1 wherein said surgical head is operated so that said recess extends only partially through the myocardium tissue from the left ventricle of the patient.

16. A cardiovascular treatment method comprising the steps of:

providing an elongate flexible surgical instrument having a distal end;

inserting a distal end portion of said instrument into a vascular system of a patient;

disposing a surgical head at said distal end of said instrument so that said head is disposed inside a coronary vessel adjacent to myocardium tissue of the patient;

operating said head inside said coronary vessel to form a recess in the myocardium tissue; and prior to operating said head to form said recess, measuring a thickness of the myocardium tissue, said recess having a length determined in accordance with the measured thickness of the myocardium tissue.

17. The method set forth in claim 16 wherein measuring said thickness includes a step taken from the group consisting essentially of:

operating an ultrasonic sensing system;

operating a magnetic resonance imaging machine;

operating a computer aided tomography scanning machine; and taking an echocardiogram.

18. The method set forth in claim 17 wherein said head is operated for a limited time to ensure that said recess terminates in the myocardium tissue.

19. The method set forth in claim 16 wherein the operating of said surgical head is implemented during diastole.

20. The method set forth in claim 19, further comprising operating a computer to synchronize the operating of said surgical head with the rhythm of said heart.

* * * * *